United States Patent [19]

Vincent

[11] Patent Number: 5,160,338
[45] Date of Patent: Nov. 3, 1992

[54] DEVICE FOR REMOVING IMPLANTABLE ARTICLES

[75] Inventor: Vernon L. Vincent, Santa Barbara, Calif.

[73] Assignee: INAMED Development Co., Carpinteria, Calif.

[21] Appl. No.: 792,030

[22] Filed: Nov. 13, 1991

[51] Int. Cl.$^5$ .................. A61B 17/08; A61B 17/00; A61F 2/02
[52] U.S. Cl. ........................... 606/157; 606/228; 600/3; 623/11
[58] Field of Search ............ 606/120, 138, 151–153, 606/157, 158, 228; 623/11, 12; 600/3–5, 29–31; 128/DIG. 25

[56] References Cited

U.S. PATENT DOCUMENTS

| | | | |
|---|---|---|---|
| 3,856,017 | 12/1974 | Perisse et al. | 606/157 X |
| 4,592,339 | 6/1986 | Kuzmak et al. | 606/157 X |
| 4,950,276 | 8/1990 | Vince | 606/157 X |
| 5,074,868 | 12/1991 | Kuzmak | 606/157 |

Primary Examiner—Ronald Frinks
Attorney, Agent, or Firm—Michael G. Petit

[57] ABSTRACT

A device facilitating remote removal of an article implanted beneath the skin. In one embodiment, the implantable article comprises a band which is operatively placed to encircle an organ such as the stomach. Once in position, the band is tightened and held securely with sutures thereby preventing the stomach-encircling band from opening. If, following implantation, it becomes necessary or desirable to remove the band, a remotely actuated releasing wire, the end of which wire is implanted at an accessible site beneath the subcutaneous tissue permits the removal of the band without major surgery. In one embodiment, the sutures securing the band in an encircling position are conveniently removed by means of a wire within the band which wire, when retracted by remote activation, releases the retaining sutures and frees the band for removal. Actual removal of the released band is accomplished by pulling the band out of the abdomen and through the superficial incision by means of the wire.

2 Claims, 1 Drawing Sheet

DEVICE FOR REMOVING IMPLANTABLE ARTICLES

BACKGROUND OF THE INVENTION

1. Field of the Invention

The present invention relates to a device providing means for the remote removal of an implantable article. The device permits the removal of an implanted article from within the abdominal cavity without the necessity of major surgery.

2. Reference to Co-pending Patent Applications

Reference is made to co-pending patent application, Ser. No. 07/562,391, filed Aug. 3, 1990, now U.S. Pat. No. 5,074,868 entitled Reversible Stoma Adjustable Gastric Band naming Lubomyr I. Kuzmak as the inventor and having a common assignee with the present application.

3. Description of the Prior Art

The need for the current invention is readily understood by discussing an exemplary implantable article such as a gastric band. Morbid obesity is a condition that is associated with a multitude of other hazards to health that include socio-psychologic problems and reduced life expectancy. Dietary management of morbid obesity has not been successful as a long term treatment. Psychiatric or dietary regimens depend upon the willpower of the patient to achieve the desired results. While weight loss may occur, the lack of willpower in patients often leads to ultimate failure. In response to the failure of dietary management, various surgical techniques have been developed and used to try to treat morbid obesity.

A promising method of treating morbid obesity employs the placement of a band around a portion of the stomach thereby compressing the stomach and creating a stoma opening that is less than the normal interior diameter of the stomach for restricting food intake into the lower digestive portion of the stomach. Such a band has been described by Kuzmak et al in U.S. Pat. No. 4,592,339. It comprises a substantially non-extensible belt-like strap which constrictively encircles the outside of the stomach thereby preventing the stoma opening from expanding. Kuzmak et al also describe bands which include a balloon-like section that is expandable and deflatable through a remote injection site. The balloon-like expandable section is used to adjust the size of the stoma opening both intraoperatively and post-operatively. Such a device is referred to as a stoma-adjustable gastric band.

Complications have been observed with both inflatable and non-inflatable gastric bands. In particular, obstruction of the stoma from edema and migration of the band has been observed. Such edema-caused obstruction of the stoma may be due to excessive vomiting. In these cases, the stoma must be enlarged either by deflating the expandable portion of a band or by removing the band altogether.

It is desirable to provide a gastric banding device with means thereon for removal of the band without the necessity for major surgery. An implantable device with such means for removal is referred to hereinafter as a reversible implantable device. Kuzmak, in pending U.S. Patent application Ser. No. 07/562,391 filed Aug. 3, 1990 the contents of which are incorporated herein by references, describes a reversing mechanism for removal of an implantable gastric band comprising a wire actuated blade which severs the retaining sutures. The moveable blade slides in a track within the band in response to traction on the actuating (releasing) wire thereby severing retaining sutures in its path. The assembly is expensive to build and requires great traction (with great resulting stress on the wire) to slide the blade, guillotine fashion, in its track. A simpler mechanism requiring minimal tension to actuate is desirable.

SUMMARY OF THE INVENTION

It is an object of this invention to provide a simple and inexpensive means for removing an implanted article.

It is yet another object of this invention to enable the remote activation of such means for removal.

It is yet another object of this invention is to provide a device for the remote removal of an implanted article which requires little force to operate.

DETAILED DESCRIPTION OF THE PREFERRED EMBODIMENTS

Figure 1:
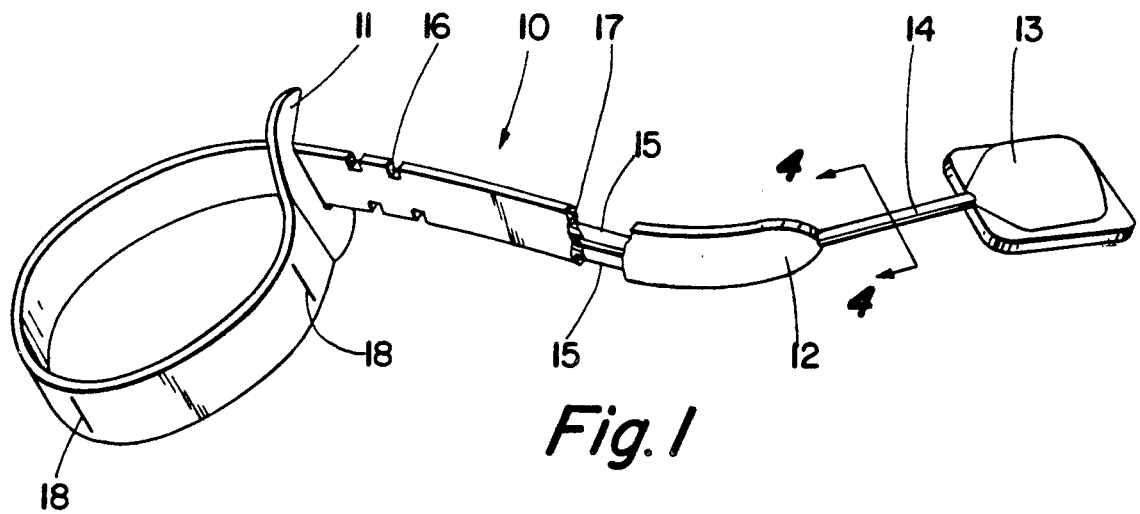
FIG. 1 is a perspective view of a band-shaped reversible article containing a removal device according to the present invention.
Figure 4:
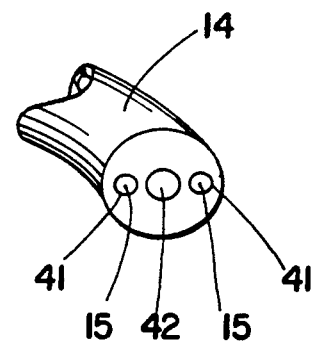
FIG. 4 is a cross-sectional view of the conduit of FIG. 1 along line 4—4.

The description of the preferred embodiment of the present invention is best understood by considering an implantable article such as a gastric band which, following implantation, may need to be removed in combination with the device of the present invention. Turning now to FIG. 1, a reversible gastric band, generally indicated at 10, is shown which is suitable for implantation in an encircling position around the stomach. The band has a buckle end 11 and a free end 12. A conduit 14, generally made from a biocompatible material such as silicone, houses one or more suture retaining wires 15 within one or more lumens (41, 42 FIG. 4) within the conduct. An injection port 13 in fluid communication with an inflatable member (not shown) within the band 10 may optionally be present.

Figure 2:
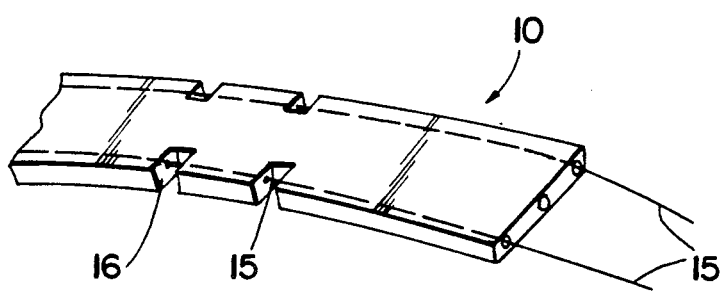
FIG. 2 is a blown-up perspective view of the removal device housed within the implantable band-shaped article of FIG. 1.

Suture retaining slots 16 cut into the edge of the band transect the suture retaining wires within the band and extend beyond the suture-retaining wire(s) 15 toward the center of the band. This is shown more clearly in FIG. 2 where the wires 15 are shown passing through the slots 16. Suturing slots 18 are conveniently placed in the band to facilitate suturing the band in an encircling position.

Figure 3:
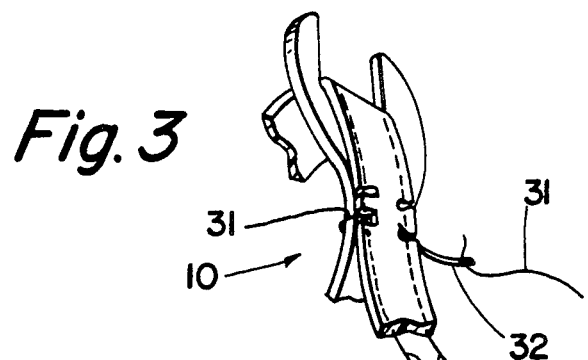
FIG. 3 shows the implantable band-shaped article secured in an encircling position within the body by means of sutures or ligatures.

Turning now to FIG. 3, the band 10 is guided into an encircling position around the stomach (not shown) and tightened. Once the desired size is obtained a suture 31 can easily be passed through the suture-retaining slot 16 by means of a needle 32. The suture 31 is passed through the suture slot 18 and around the suture-retaining wire 15 and securely tied. The band is thus held in the encircling position around the stomach.

The suture-retaining wires(s) 15 are led from suture-retaining wire lumen(s) 17 within the band into suture-retaining wire lumens 41 within the conduit. The end of the conduit opposite the band 10 (the distal end) is then threaded up beneath the skin and implanted subcutaneously. To remove the band, the distal end of the conduit is exposed by minor surgery. The suture-retaining wire(s) 15 contained within the conduit are grasped and pulled until the suture-retaining wire is clear of the suture-retaining slots 16 thereby releasing the sutures and enabling the band to open. Once the band is released, it may be pulled out through the exposing excision by pulling on the conduit. It is understood that the use of a suture to secure the band is exemplary. A ligature of any biocompatible material such as a stainless steel staple or a clip ring can also be used to lock the band into an encircling position.

Figure 5:
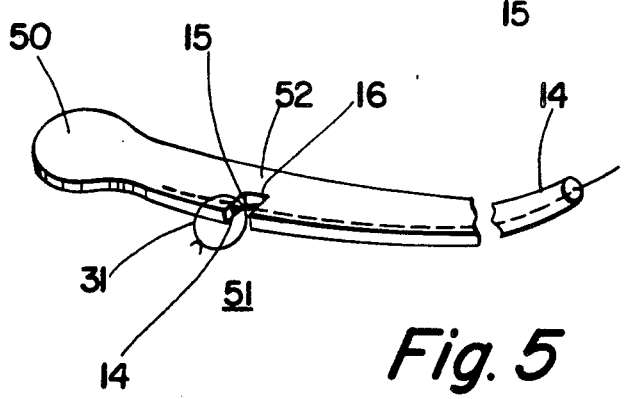
FIG. 5 shows a perspective view of a second preferred embodiment of the invention.

While the invention has been described in terms of its use with a particular article, it is appreciated by one skilled in the art that many other articles and configurations are possible within the scope of the invention. For example, the suture-retaining slot and suture-retaining wire may be used to reversible anchor any device in position within the body as shown in FIG. 5. A device or article 50 contains a reversible portion 52 which is anchored to surrounding tissue 51 by means of a ligature 31 passed around the guide wire 15 to assure that the article 50 does not move following implantation. This would be particularly desirable, for example, if the article 50 were filled with a radioactive material suitable for applying therapeutic doses of radiation to cancerous tissue. The distal end of the conduit 14 can be similarly implanted beneath the skin. A slot 16 connects the guidewire lumen 41 with the exterior surface of the reversible portion. When it is desired to remove the article 50, withdrawing the suture-retaining guidewire from the suture-retaining slot 16 will free the suture from the reversible portion and the article or device may be easily removed by traction on the conduit.

Although the present invention has been described with reference to preferred embodiments, workers skilled in the art will recognize that changes may be made in form and detail without departing from the spirit and scope of the invention.

What I claim is:

1. A reversible implantable device, a portion of said device comprising a reversible portion having an exterior surface and an interior which may be anchored within the body by means of one or more ligatures passed therethrough, said reversible portion comprising a wire guiding lumen housed within the interior portion, a suture-retaining wire passing through the wire guiding lumen, and at least one slot connecting said wire guiding lumen to the exterior surface of said reversible portion.

2. The reversible implantable device of claim 1 wherein said slot connecting the wire guiding lumen to the exterior surface of the reversible portion is dimensioned to accommodate a ligature therewithin.

* * * * *